United States Patent
Elder et al.

(10) Patent No.: US 9,274,098 B2
(45) Date of Patent: Mar. 1, 2016

(54) ANALYTE METER DIGITAL SAMPLE DETECTION

(71) Applicant: LifeScan Scotland Limited, Inverness, Inverness-shire (GB)

(72) Inventors: David Elder, Inverness (GB); Stanley Young, Inverness (GB); Ciaran Carney, Inverness (GB); Brian Guthrie, Inverness (GB); Steven Milne, Inverness (GB); John Young, Inverness (GB)

(73) Assignee: LifeScan Scotland Limited, Inverness (GB)

( * ) Notice: Subject to any disclaimer, the term of this patent is extended or adjusted under 35 U.S.C. 154(b) by 480 days.

(21) Appl. No.: 13/874,112

(22) Filed: Apr. 30, 2013

(65) Prior Publication Data

US 2014/0318986 A1 Oct. 30, 2014

(51) Int. Cl.
*G01N 27/327* (2006.01)
*G01N 33/487* (2006.01)

(52) U.S. Cl.
CPC ...... *G01N 33/48785* (2013.01); *G01N 27/3273* (2013.01)

(58) Field of Classification Search
CPC .......... G01N 27/3271; G01N 27/3272; G01N 27/3274; G01N 33/48785
See application file for complete search history.

(56) References Cited

U.S. PATENT DOCUMENTS

| 2005/0045476 | A1 | 3/2005 | Neel et al. |
| 2009/0255810 | A1* | 10/2009 | Ichino ............... G01N 33/48785 204/403.02 |
| 2009/0280551 | A1 | 11/2009 | Cardosi et al. |
| 2009/0301899 | A1 | 12/2009 | Hodges et al. |
| 2010/0108508 | A1 | 5/2010 | Manabe et al. |

FOREIGN PATENT DOCUMENTS

| WO | WO 2013/098563 A1 | 7/2013 |
| WO | WO 2013/098565 A1 | 7/2013 |

OTHER PUBLICATIONS

Explantion of a pull down resistor downloaded on Oct. 9, 2015 from http://www.resistorguide.com/pull-up-resistor_pull-down-resistor/.*
European Search Report issued in related European Patent Application No. 14166463.1, dated Sep. 10, 2014, 7 pages.

* cited by examiner

*Primary Examiner* — Alexander Noguerola

(57) ABSTRACT

An analyte meter is configured to digitally test for the presence of a test strip in the meter and for the presence of a sample in the test strip prior to activating an analog current measurement circuit of the meter. A test strip port connector having a plurality of contacts receives an inserted test strip in which the contacts electrically connect to electrodes on the test strip for digitally detecting both the presence of a test strip and a sample added to the test strip. A control circuit monitoring the contacts maintains the analyte meter in a low power mode until detecting both the test strip and the sample, whereupon the control circuit activates the meter and enables an analog analyte measurement circuit.

16 Claims, 4 Drawing Sheets

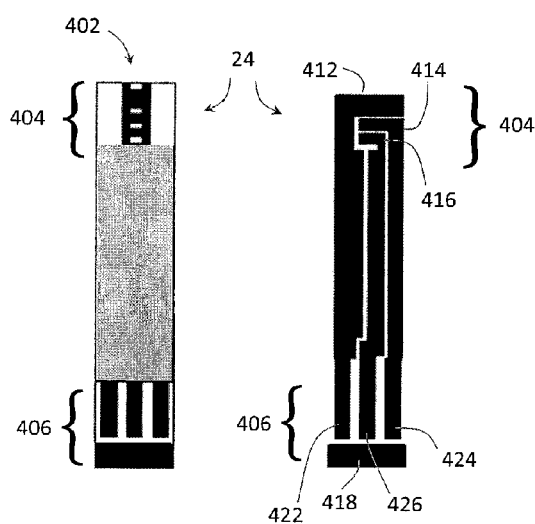
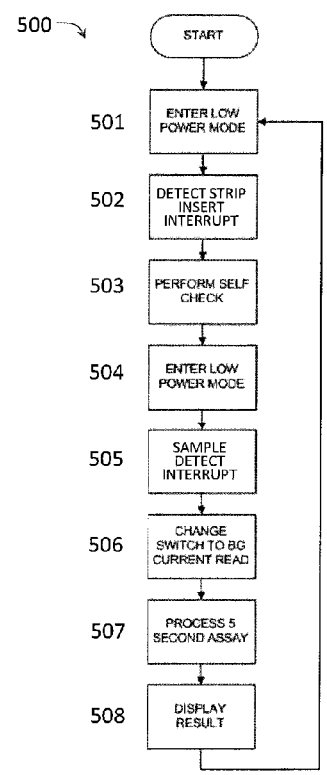
FIG. 4A    FIG. 4B
FIG. 5

ANALYTE METER DIGITAL SAMPLE DETECTION

TECHNICAL FIELD

This application generally relates to the field of blood analyte measurement systems and more specifically to portable analyte meters that are configured to digitally detect an insertion of a test strip and to digitally detect application of a blood sample to the test strip before activating power consuming analog subsystems of the analyte meter.

BACKGROUND

Blood glucose measurement systems typically comprise an analyte meter that is configured to receive a biosensor, usually in the form of a test strip. Because many of these systems are portable, and testing can be completed in a short amount of time, patients are able to use such devices in the normal course of their daily lives without significant interruption to their personal routines. A person with diabetes may measure their blood glucose levels several times a day as a part of a self management process to ensure glycemic control of their blood glucose within a target range. A failure to maintain target glycemic control can result in serious diabetes-related complications including cardiovascular disease, kidney disease, nerve damage and blindness.

There currently exist a number of available portable electronic analyte measurement devices that are designed to automatically activate upon insertion of a test strip. Electrical contacts, or prongs, in the meter establish connections with contact pads on the test strip while a microcontroller in the meter determines, based on electrical signals from the test strip, whether the test strip is properly inserted. This activation typically powers the entire device, including analog components, in preparation for receiving a sample applied to the test strip from the user. The analog circuit components consume power while waiting for a sample to be applied by a user, which may take several minutes. During this waiting time the battery lifetime is shortened unnecessarily. Occasionally, users may decide not to provide a sample at all and may remove the test strip after some time, which again needlessly consumes battery power. Because analog circuits typically consume significantly more power than digital based circuits, it would be advantageous to detect the application of a sample in a test strip using a digital circuit and to delay powering on the analog circuit components until the sample is applied.

BRIEF DESCRIPTION OF THE DRAWINGS

The accompanying drawings, which are incorporated herein and constitute part of this specification, illustrate presently preferred embodiments of the invention, and, together with the general description given above and the detailed description given below, serve to explain features of the invention (wherein like numerals represent like elements).

FIGS. 4A-4B illustrate an exemplary test strip comprising contact pads and electrodes for interoperating with the blood analyte meter of FIGS. 1A-1B; and FIG. 5 illustrates a flow chart of a method of operating the blood analyte measurement system of FIGS. 1A-1B.

MODES OF CARRYING OUT THE INVENTION

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "patient" or "user" refer to any human or animal subject and are not intended to limit the systems or methods to human use, although use of the subject invention in a human patient represents a preferred embodiment.

The term "sample" means a volume of a liquid, solution or suspension, intended to be subjected to qualitative or quantitative determination of any of its properties, such as the presence or absence of a component, the concentration of a component, e.g., an analyte, etc. The embodiments of the present invention are applicable to human and animal samples of whole blood. Typical samples in the context of the present invention as described herein include blood, plasma, red blood cells, serum and suspensions thereof.

The term "about" as used in connection with a numerical value throughout the description and claims denotes an interval of accuracy, familiar and acceptable to a person skilled in the art. The interval governing this term is preferably ±10%. Unless specified, the terms described above are not intended to narrow the scope of the invention as described herein and according to the claims.

Figure 1A:
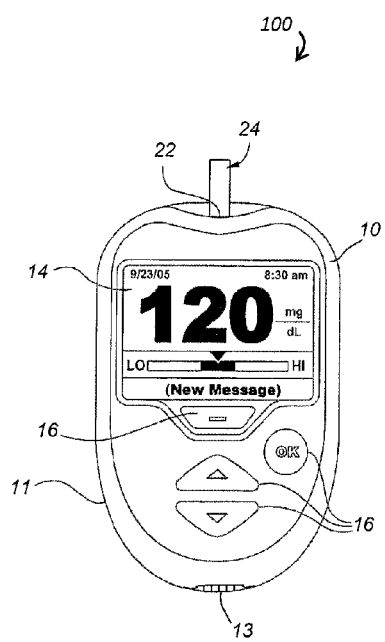
FIG. 1A illustrates a diagram of an exemplary test strip based blood analyte measurement system.

FIG. 1A illustrates an analyte measurement system 100 that includes an analyte meter 10. The analyte meter 10 is defined by a housing 11 that retains a data management unit 140 and further includes a strip port opening 22 sized for receiving a biosensor. According to one embodiment, the analyte meter 10 may be a blood glucose meter and the biosensor is provided in the form of a glucose test strip 24 inserted into strip port opening 22 for performing blood glucose measurements. The analyte meter 10 further includes a data management unit 140, FIG. 1B, disposed within the interior of the meter housing 11, a plurality of user interface buttons 16, and a display 14 as illustrated in FIG. 1A. A predetermined number of glucose test strips may be stored in the housing 11 and made accessible for use in blood glucose testing. The plurality of user interface buttons 16 can be configured to allow the entry of data, to prompt an output of data, to navigate menus presented on the display 14, and to execute commands. Output data can include values representative of analyte concentration presented on the display 14. Input information, which is related to the everyday lifestyle of an individual, can include food intake, medication use, occurrence of health check-ups, and general health condition and exercise levels of an individual. These inputs can be requested via prompts presented on the display 14 and can be stored in a memory module of the analyte meter 10. Specifically and according to this exemplary embodiment, the user interface buttons 16 include markings, e.g., up-down arrows, text characters "OK", etc, which allow a user to navigate through the user interface presented on the display 14. Although the buttons 16 are shown herein as separate switches, a touch screen interface on display 14 with virtual buttons may also be utilized.

Figure 1B:
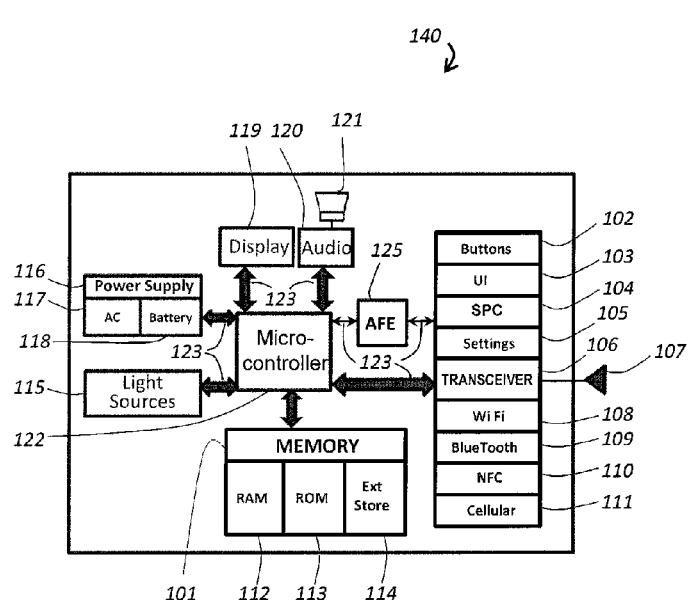
FIG. 1B illustrates a diagram of an exemplary processing system of the test strip based blood analyte measurement system of FIG. 1A.

The electronic components of the analyte measurement system 100 can be disposed on, for example, a printed circuit board situated within the housing 11 and forming the data management unit (DMU) 140 of the herein described system. FIG. 1B illustrates, in simplified schematic form, several of the electronic subsystems disposed within the housing 11 for purposes of this embodiment. The data management unit 140 includes a processing unit 122 in the form of a microprocessor, a microcontroller, an application specific integrated circuit ("ASIC"), a mixed signal processor ("MSP"), a field programmable gate array ("FPGA"), or a combination thereof, and is electrically connected to various electronic modules included on, or connected to, the printed circuit board, as will be described below. The processing unit 122 is electrically connected to, for example, a test strip port connector 104 ("SPC") via a Strip Measurement Front End ("SMFE") subsystem 125, described in more detail below with reference to FIG. 2. The SMFE circuit 125 is electrically connected to the strip port connector 104 during blood glucose testing. To measure a selected analyte concentration, the SMFE circuit 125 detects a resistance across electrodes of analyte test strip 24 having a blood sample disposed thereon, using a potentiostat, and converts an electric current measurement into digital form for presentation on the display 14. The processing unit 122 can be configured to receive input from the strip port connector 104, SMFE subsystem 125, and may also perform a portion of the potentiostat function and the current measurement function.

The analyte test strip 24 can be in the form of an electrochemical glucose test strip. The test strip 24 can include one or more working electrodes at one end of the test strip 24. Test strip 24 can also include a plurality of electrical contact pads at a second end of the test strip 24, where each electrode can be in electrical communication with at least one electrical contact pad, as described below in relation to FIGS. 4A and 4B. Strip port connector 104 can be configured to electrically interface to the electrical contact pads and form electrical communication with the electrodes. Test strip 24 can include a reagent layer that is disposed over one or more electrodes within the test strip 24. The reagent layer can include an enzyme and a mediator. Exemplary enzymes suitable for use in the reagent layer include glucose oxidase, glucose dehydrogenase (with pyrroloquinoline quinone co-factor, "PQQ"), and glucose dehydrogenase (with flavin adenine dinucleotide co-factor, "FAD"). An exemplary mediator suitable for use in the reagent layer includes ferricyanide, which in this case is in the oxidized form. The reagent layer can be configured to physically transform glucose into an enzymatic by-product and in the process generate an amount of reduced mediator (e.g., ferrocyanide) that is proportional to the glucose concentration. The working electrode can then be used to measure a concentration of the reduced mediator in the form of a current. In turn, microcontroller 122 can convert the current magnitude into a glucose concentration. An exemplary analyte meter performing such current measurements is described in U.S. Patent Application Publication No. US 1259/0301899 A1 entitled "System and Method for Measuring an Analyte in a Sample", which is incorporated by reference herein as if fully set forth in this application.

A display module 119, which may include a display processor and display buffer, is electrically connected to the processing unit 122 over the communication interface 123 for receiving and displaying output data, and for displaying user interface input options under control of processing unit 122. The structure of the user interface, such as menu options, is stored in user interface module 103 and is accessible by processing unit 122 for presenting menu options to a user of the blood glucose measurement system 100. An audio module 120 includes a speaker 121 for outputting audio data received or stored by the DMU 140. Audio outputs can include, for example, notifications, reminders, and alarms, or may include audio data to be replayed in conjunction with display data presented on the display 14. Such stored audio data can be accessed by processing unit 122 and executed as playback data at appropriate times. A volume of the audio output is controlled by the processing unit 122, and the volume setting can be stored in settings module 105, as determined by the processor or as adjusted by the user. User input module 102 receives inputs via user interface buttons 16 which are processed and transmitted to the processing unit 122 over the communication interface 123. The processing unit 122 may have electrical access to a digital time-of-day clock connected to the printed circuit board for recording dates and times of blood glucose measurements, which may then be accessed, uploaded, or displayed at a later time as necessary.

The display 14 can alternatively include a backlight whose brightness may be controlled by the processing unit 122 via a light source control module 115. Similarly, the user interface buttons 16 may also be illuminated using LED light sources electrically connected to processing unit 122 for controlling a light output of the buttons. The light source module 115 is electrically connected to the display backlight and processing unit 122. Default brightness settings of all light sources, as well as settings adjusted by the user, are stored in a settings module 105, which is accessible and adjustable by the processing unit 122.

A memory module 101, that includes but are not limited to volatile random access memory ("RAM") 112, a non-volatile memory 113, which may comprise read only memory ("ROM") or flash memory, and a circuit 114 for connecting to an external portable memory device, for example, via a USB data port, is electrically connected to the processing unit 122 over a communication interface 123. External memory devices may include flash memory devices housed in thumb drives, portable hard disk drives, data cards, or any other form of electronic storage devices. The on-board memory can include various embedded applications and stored algorithms in the form of programs executed by the processing unit 122 for operation of the analyte meter 10, as will be explained below. On board memory can also be used to store a history of a user's blood glucose measurements including dates and times associated therewith. Using the wireless transmission capability of the analyte meter 10 or the data port 13, as described below, such measurement data can be transferred via wired or wireless transmission to connected computers or other processing devices.

A wireless module 106 may include transceiver circuits for wireless digital data transmission and reception via one or more internal digital antennas 107, and is electrically connected to the processing unit 122 over communication interface 123. The wireless transceiver circuits may be in the form of integrated circuit chips, chipsets, programmable functions operable via processing unit 122, or a combination thereof. Each of the wireless transceiver circuits is compatible with a different wireless transmission standard. For example, a wireless transceiver circuit 108 may be compatible with the Wireless Local Area Network IEEE 802.11 standard known as WiFi. Transceiver circuit 108 may be configured to detect a WiFi access point in proximity to the analyte meter 10 and to transmit and receive data from such a detected WiFi access point. A wireless transceiver circuit 109 may be compatible with the Bluetooth protocol and is configured to detect and process data transmitted from a Bluetooth "beacon" in proximity to the analyte meter 10. A wireless transceiver circuit 110 may be compatible with the near field communication ("NFC") standard and is configured to establish radio communication with, for example, an NFC compliant point of sale terminal at a retail merchant in proximity to the analyte meter 10. A wireless transceiver circuit 111 may comprise a circuit for cellular communication with cellular networks and is configured to detect and link to available cellular communication towers.

A power supply module 116 is electrically connected to all modules in the housing 11 and to the processing unit 122 to supply electric power thereto. The power supply module 116 may comprise standard or rechargeable batteries 118 or an AC power supply 117 may be activated when the analyte meter 10 is connected to a source of AC power. The power supply module 116 is also electrically connected to processing unit 122 over the communication interface 123 such that processing unit 122 can monitor a power level remaining in a battery power mode of the power supply module 116.

Figure 2:
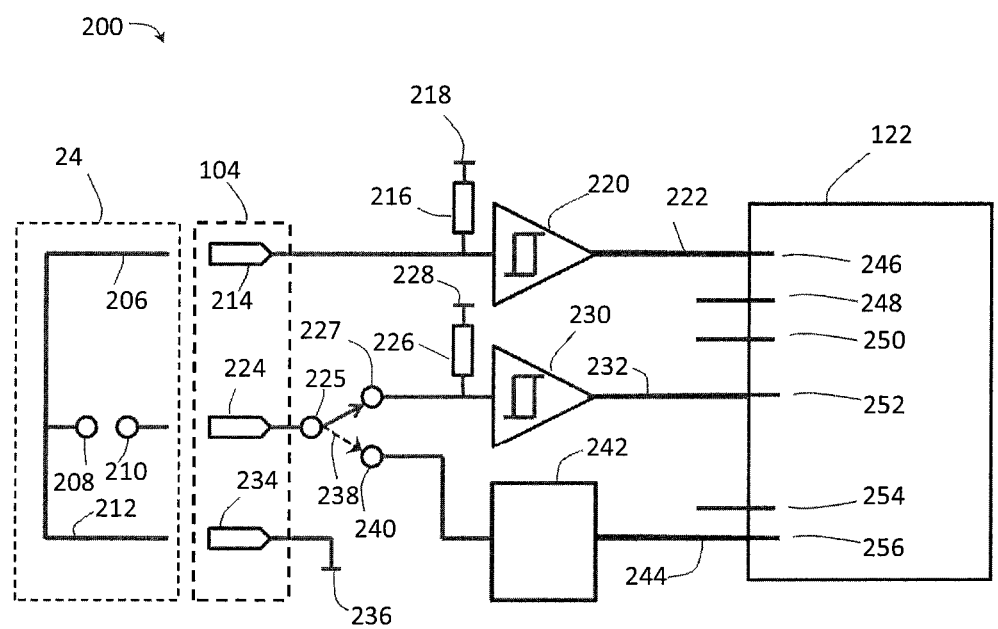
FIG. 2 illustrates a schematic diagram of the analyte meter and test strip inserted therein.

With reference to FIG. 2, there is illustrated in more detail pertinent portions of the test strip 24, SPC 104, and the front-end subsystem 125 which is connected between the SPC 104 and the microcontroller 122, as described above. The test strip 24, as shown, includes electrodes 206 and 212 for electrically connecting with the SPC strip-detect contact 214 and ground reference contact 234, respectively, when the test strip 24 is inserted into the strip port opening 22. A pair of blood sample electrodes 208, 210 in the test strip remain in an open circuit condition until a blood sample is applied to the test strip, wherein the blood sample physically bridges the electrodes 208 and 210 and becomes an electrical current conduction path between them. One of these electrodes 210 is electrically connected to the SPC sample detect/working contact 224 when the test strip 24 is inserted into the strip port opening 22. Although embodiments of the SPC 104 may include other electrical contacts for electrically connecting to additional electrodes of the test strip 24, such as hematocrit measurement electrodes, for example, which transmit signals to microcontroller 122 input pins 248, 250, and an additional working electrode which transmits signals to microcontroller 122 input pin 254, their description is omitted herein for purposes of clarity in the Figures.

During the low power mode, the strip-detect output 222 transmits a digital high voltage level to the microcontroller 122 strip-detect interrupt input pin 246, via the Schmitt trigger 220 which has an input connected to pull up resistor 216 at about 100 kΩ, and system power supply terminal 218 at about 3 V, indicating to the microcontroller 122 that a test strip is not inserted. When the test strip 24 is inserted into strip port opening 22, test strip electrode 206 establishes an electrical connection with SPC contact 214 simultaneously with test strip electrode 212 establishing an electrical connection with SPC contact 234, which shorts SPC contact 214 to reference ground 236, thereby generating a negative going strip-detect interrupt signal transmitted to the microcontroller over the strip-detect output 222. This indicates to the microcontroller that a strip 24 is inserted into the strip port opening 22 whereupon the microcontroller 122 powers on the analyte meter 100 and begins a self test sequence. Similarly, the sample-detect output the 232 transmits a digital high voltage level to the microcontroller 122 sample-detect interrupt input pin 252, via the Schmitt trigger logic circuit 230 having an input connected to pull up resistor 226 at about 100-500 kΩ, and to system power supply terminal 228, indicating to the microcontroller 122 that a blood sample has not been applied to test strip 24.

After the self test sequence, which may include hardware integrity checks, calibration of impedance circuits with respect to voltage offsets and leakage currents, and the like, the microcontroller may initiate a message displayed on the meter's display 14 to request the user to apply a sample to the test strip, whereupon the analyte meter reverts to a low power mode. LCD displays known as zero power bistable LCD displays, or other low power LCD displays, may be used to reduce power consumption while still displaying the request for a sample. When a blood sample is provided to the test strip 24 by a user, the sample makes physical contact with the open circuit electrodes 208, 210 thereby closing the circuit and establishing an electrical connection with SPC contact 224 which shorts it to reference ground 236, thereby generating a negative going sample-detect interrupt signal transmitted to the microcontroller over the sample-detect output 232.

In response to receiving the sample-detect interrupt signal, microcontroller 122 energizes the blood glucose measurement circuit 242 and electronically activates switch 225 to connect SPC contact 224 to blood glucose measurement circuit input 240, thereby connecting the blood glucose measurement electrodes 208, 210 of the test strip 24 to the blood glucose current measurement circuit 242, whereupon a blood glucose assay begins. Without implementation of the digital sample-detect circuit described herein, the SPC contact 224 may be permanently connected via electrical connection 238 to the blood glucose measurement circuit 242 via circuit input 240. Thus, in one embodiment, the addition of electronic switch 225, pull-up resistor 226, and Schmitt trigger 230, to provide a digital sample-detect input 232 to microcontroller 122 avoids power draining activation of the blood glucose measurement circuit 242 before an actual sample is added to the inserted test strip.

Figure 3:
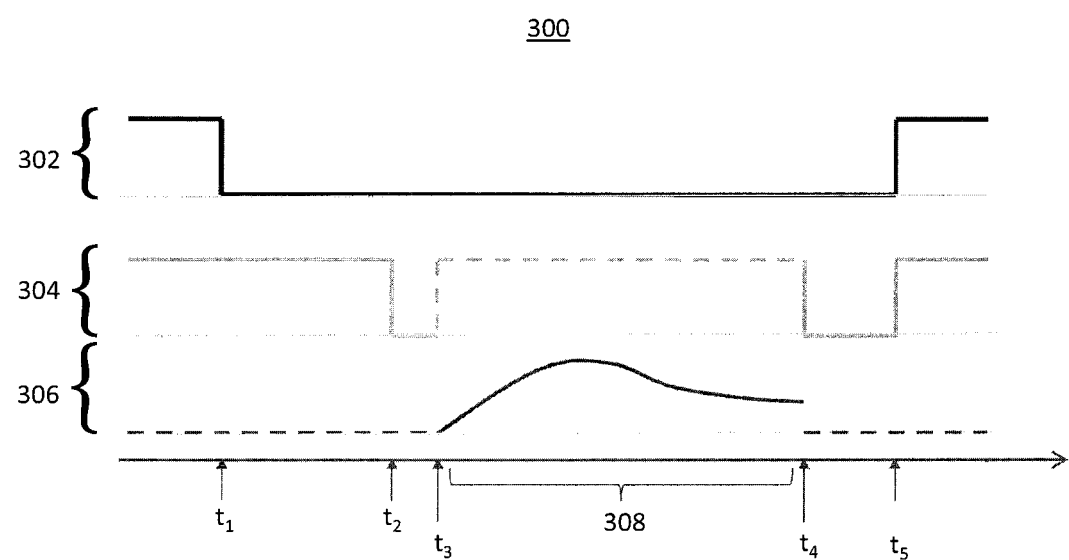
FIG. 3 illustrates a timing diagram of the signals produced by the circuit schematic of FIG. 2.

FIG. 3 demonstrates a timing diagram 300 of some of the electrical signals just described. The strip-detect signal 302, received at microcontroller pin 246 via SPC contact 214, is shown as generating the negative going strip detect interrupt at time $t_1$. The negative going sample-detect signal 304, received at microcontroller pin 252 via SPC contact 224 through switch position 227, is shown at time $t_2$. The microcontroller 122 may establish a time limit, between $t_1$ and $t_2$, e.g. two minutes, for the user to apply the blood sample. If the time limit expires, the microcontroller may be programmed to switch the meter into the low power "sleep" mode. The sample-detect interrupt at time $t_2$ signals the microcontroller 122 that the assay of the blood sample may begin, wherein the microcontroller switches the electronic switch 225 to connect the SPC contact 224, and thereby the electrode 210, to the blood glucose current measurement circuit input 240 at time $t_3$. The blood glucose current level 306 as measured by the standard blood glucose current measurement circuit 242, starting at time $t_3$ until time $t_4$, is received at microcontroller input pins 254, 256, illustrating the performance of an assay 308 for about five seconds. At time $t_4$ the analog blood glucose measurement circuit 242 is turned off and the switch 225 reconnects the sample-detect contact 224 to the sample-detect circuit input 227. After the blood glucose current measurement 308 is completed and the results displayed to the user, the user removes the test strip 24 from the test strip port connector 104 at time $t_5$ and, in response, the microcontroller 122 returns the meter to low power mode. The dashed line portions of signals 304, 306 indicate time durations during which the microcontroller 122 does not monitor their voltage levels.

With reference to FIGS. 4A-4B, there are illustrated exemplary diagrams of the test strip 24. FIG. 4A illustrates an exterior view of the test strip 24 having an inlet 402 for receiving a sample at a distal end 404 of the test strip 24, while a plurality of electrical contact pads are disposed at a proximal end 406 of the test strip 24, which is inserted into the test strip port connector 104. A plurality of electrodes extend from the contact pads at the proximal end 406 of the test strip 24 to the distal end 404 of the test strip 24 and include a counter (reference) electrode 412 electrically connected to counter electrode pad 422; a first working electrode 414 electrically connected to a first electrode contact pad 424, a second working electrode 416 electrically connected to a second working electrode contact pad 426; and a strip-detect contact pad 418. Electrical contacts formed as prongs in the SPC 104 of the analyte meter 10 electrically connect with the contact pads 418-426 of the test strip when the test strip is inserted in the SPC and thereby are electrically connected to their corresponding electrodes, but for contact pad 418 which does not have a corresponding electrode. This allows electrical communication between the microcontroller 122 and the test strip electrodes 412-416, as described above.

When the test strip 24 is inserted in the test strip port connector 104, the prongs, 214, 224, and 234 of the SPC 104 are connected to the test strip contact pads as follows: strip-detect contact 214 is connected to contact pad 418; sample-detect contact 224 is connected to either the first 414 or second 416 working electrode; and reference contact 234 is connected to both the contact pad 418 and the counter (reference) contact 422. As explained above, the strip-detect signal 302 is generated thereby. When a blood sample is applied and received in blood sample inlet 402, it physically associates with counter (reference) electrode 412, the first working electrode 414, and the second working electrode 416, forming an electrical connection between the three electrodes. As explained above, the sample-detect signal 304 is generated thereby and the meter is switched, via microcontroller 122 connecting switch 225 to the blood glucose measurement circuit input 240, placing the meter into an active mode and activating the analog blood glucose measurement circuit 242. A controlled glucose current traveling through the blood sample may then be measured by the analyte measurement system 100, as described above. Exemplary embodiments of analyte meters employing test strips having various configurations of contact pads and electrodes are described in PCT Patent Application PCT/GB2012/053279 entitled "Accurate Analyte Measurements for Electrochemical Test Strip Based on Sensed Physical Characteristic(s) of the Sample Containing the Analyte and Derived BioSensor Parameters" and PCT Patent Application PCT/GB2012/053276 entitled "Accurate Analyte Measurements for Electrochemical Test Strip Based on Sensed Physical Characteristic(s) of the Sample Containing the Analyte", both of which patent applications are incorporated by reference herein as if fully set forth herein.

A method of operation of one embodiment of the analyte meter 100 is illustrated in the flow chart 500 of FIG. 5. The analyte measurement system 100 normally runs under power from a set of contained batteries (not shown) in a low power "sleep" mode, as in step 501. At step 502, the insertion of a test strip is detected by microcontroller 122 which then powers on portions of the analyte meter 10 for performing a self check at step 503, as described above. At this point an incentive message may be displayed on the meter display 14 requesting a user to apply a sample to the test strip, whereupon the analyte meter 10 reverts to a low power mode, at step 504, which prevents the analog blood glucose measurement circuitry from drawing excessive power while the meter waits to receive the sample detect interrupt signal. Upon detecting a sample applied to the test strip at step 505, the blood glucose contact 224 is electronically switched over to the input 240 of the standard analog blood glucose current measurement circuit 242, at step 506, and an assay is performed as in the normal course at step 507. Without implementing the embodiment of the analyte meter 10 disclosed herein, the glucose current contact 224 is normally permanently connected to the blood glucose current measurement circuit 242. Finally, at step 508, the analyte measurement result is presented on display 14, and the meter is returned to the low power mode.

In terms of operation, one aspect of the analyte meter 10 may include a digital capability for detecting insertion of a test strip 24 into strip port connector 104 intended for use in the analyte meter 10. Additional digital circuits are used to further detect the application of a blood sample before activating the analog blood glucose current measurement subsystem which consumes significantly more power than the digital electronic components.

As will be appreciated by one skilled in the art, aspects of the present invention may be embodied as a system, method, or computer program product. Accordingly, aspects of the present invention may take the form of an entirely hardware embodiment, an entirely software embodiment (including firmware, resident software, micro-code, etc.), or an embodiment combining software and hardware aspects that may all generally be referred to herein as a "circuit," "circuitry," "module," "subsystem" and/or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible, non-transitory medium that can contain, or store a program for use by or in connection with an instruction execution system, apparatus, or device.

Program code and/or executable instructions embodied on a computer readable medium may be transmitted using any appropriate medium, including but not limited to wireless, wireline, optical fiber cable, RF, etc., or any suitable combination of the foregoing.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Furthermore, the various methods described herein can be used to generate software codes using off-the-shelf software development tools. The methods, however, may be transformed into other software languages depending on the requirements and the availability of new software languages for coding the methods.

PARTS LIST FOR FIGS. 1A-5

10 analyte meter
11 housing, meter
13 data port
14 display
16 user interface buttons
22 strip port opening
24 test strip
100 analyte measurement system
101 memory module
102 buttons module
103 user interface module
104 strip port connector
105 microcontroller settings module
106 transceiver module
107 antenna
108 WiFi module
109 Bluetooth module
110 NFC module
111 GSM module
112 RAM module
113 ROM module
114 external storage
115 light source module
116 power supply module
117 AC power supply
118 battery power supply
119 display module
120 audio module
121 speaker
122 microcontroller (processing unit)
123 communication interface
125 Strip Measurement Front End (SMFE) subsystem
140 data management unit
200 digital sample detect circuit
206 test strip electrode
208 test strip sample electrode
210 test strip sample electrode
212 test strip electrode
214 SPC strip-detect contact
216 pull-up resistor
218 voltage supply
220 Schmitt trigger
222 strip-detect input
224 SPC sample-detect contact
225 electronic switch
226 pull-up resistor
227 sample detect circuit input
228 voltage supply
230 Schmitt trigger
232 sample-detect input
234 SPC reference ground contact
236 reference ground
238 connection to blood glucose measurement circuit
240 input to blood glucose measurement circuit
242 blood glucose measurement circuit
244 blood glucose measurement input
246 strip-detect input pin
248 hematocrit measurement input pin
250 hematocrit measurement input pin
252 sample-detect input pin
254 working electrode input pin
256 working electrode input pin
300 timing diagram of voltage signals and current measurement
302 strip-detect signal
304 sample-detect signal
306 glucose current level
308 blood glucose assay time
402 sample inlet
404 distal end—electrodes
406 proximal end—contact pads
412 counter (reference) electrode
414 first working electrode
416 second working electrode
418 contact pad
422 counter (reference) electrode contact pad
424 first working electrode contact pad
426 second working electrode contact pad
500 method of operating analyte meter
501 step—enter low power mode
502 step—detect strip insert interrupt
503 step—perform self check
504 step—enter low power mode
505 step—sample detect interrupt
506 step—switch to blood glucose current measurement
507 step—process assay
508 step—display result of assay While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well.

What is claimed is:

1. An analyte meter comprising:
an strip port opening configured for receiving a test strip, the strip port opening extending to a strip port connector configured to electrically connect to electrodes disposed on the test strip when the test strip is inserted into the strip port opening, said strip port connector comprising:
a first contact for detecting a digital strip-detect signal when the test strip is inserted into the strip port opening; and
a second contact for detecting a digital sample-detect signal when a sample is applied to the inserted test strip; and
a control circuit electrically connected to the first and second contacts, the control circuit being configured to maintain the analyte meter in a low power mode in the absence of detecting both the digital strip-detect signal and the digital sample-detect signal.

2. The analyte meter of claim 1, wherein the second contact is coupled to an electronic switch for electrically connecting the second contact to a sample-detect input of the control circuit when the analyte meter is in the low power mode, the electronic switch being controllable by the control circuit.

3. The analyte meter of claim 2, wherein the second contact is coupled to the electronic switch for electrically connecting the second contact to a an analyte current measurement circuit when the control circuit detects both the digital strip-detect signal and the digital sample-detect signal, and wherein the control circuit switches the analyte meter to an active mode.

4. The analyte meter of claim 1, wherein the digital strip-detect signal and the digital sample-detect signal each comprise a falling voltage generated by connecting each of the first and second contacts to a different pull-up resistor.

5. The analyte meter of claim 4, wherein said strip port connector further comprise a ground contact, and wherein the digital strip-detect signal and the digital sample-detect signal each comprise a falling voltage generated by connecting each of the first and second contacts to the ground contact.

6. The analyte meter of claim 5, wherein said electrodes disposed on the test strip comprise a pair of electrodes configured to be electrically connected only by the sample that is applied to the inserted test strip.

7. The analyte meter of claim 6, wherein one of said pair of electrodes disposed on the test strip is coupled to the ground contact and the other of said electrodes is coupled to the second contact when the test strip is inserted into the strip port opening.

8. A method of operating an analyte meter having a strip port opening configured for receiving a test strip inserted therein, the method comprising:
   maintaining the analyte meter in a low power inactive mode in the absence of a test strip being inserted in the strip port opening;
   detecting a digital strip-detect signal at a first interrupt contact of the analyte meter indicating that a test strip is inserted into the strip port opening;
   monitoring a second interrupt contact of the analyte meter to detect a digital sample-detect signal indicating that a blood sample is applied to the inserted test strip; and
   placing the analyte meter in an active mode, thereby activating an analyte current measuring circuit in the analyte meter in response to detecting the sample-detect signal.

9. The method of claim 8, wherein said detecting the digital strip-detect signal at the first interrupt contact comprises detecting a voltage drop at the first interrupt contact, the voltage drop at the first interrupt contact being caused by the test strip electrically connecting the first interrupt contact to a ground contact when the test strip is inserted in the strip port opening.

10. The method of claim 9, wherein said detecting the digital sample-detect signal at the second interrupt contact comprises detecting a voltage drop at the second interrupt contact, the voltage drop at the second interrupt contact being caused by the applied sample electrically connecting the second interrupt contact to the ground contact when the sample is applied to the inserted test strip.

11. The method of claim 10, wherein said monitoring the second interrupt contact of the analyte meter to detect the digital sample-detect signal includes resuming the low power inactive mode if the digital sample detect signal is not detected by the analyte meter within a preset time limit.

12. The method of claim 11, wherein said step of activating the analyte current measuring circuit comprises shifting an electrical connection from between the second interrupt contact and an interrupt detection circuit to between the second interrupt contact and an input to the analyte measuring circuit.

13. A digital circuit connected to a strip port opening for generating digital signals indicating both the presence of a test strip in the strip port opening and the presence of a blood sample in the test strip, the digital circuit comprising:
   a first contact electrically connected to a first pull up resistor and to a strip detect input of a control circuit;
   a second contact electrically connected to a second pull up resistor and to a sample detect input of the control circuit; and
   a third contact electrically connected to a ground, wherein the test strip is configured to electrically connect the first contact to the third contact when the test strip is inserted into the strip port opening and to electrically connect the second contact to the third contact when the blood sample is applied to the test strip.

14. The digital circuit of claim 13, wherein the electrical connection between the first contact and the third contact generates a falling voltage signal received at the strip detect input of the control circuit and the electrical connection between the second contact and the third contact generates a falling voltage signal received at the sample detect input of the control circuit.

15. The digital circuit of claim 14, wherein the test strip comprises a first electrode for connecting to the second contact when the test strip is inserted into the strip port opening and a second electrode for connecting to the third contact when the test strip is inserted into the strip port opening, and wherein a blood sample applied to the test strip electrically connects the first electrode and the second electrode.

16. The digital circuit of claim 15, further comprising an electronic switch for disconnecting the second contact from the sample detect input of the control circuit, and for connecting the second contact to a sample current measurement circuit.

* * * * *